(12) United States Patent
Yu

(10) Patent No.: US 10,722,210 B2
(45) Date of Patent: Jul. 28, 2020

(54) METHOD FOR MEMORABLE IMAGE GENERATION FOR ANONYMIZED THREE-DIMENSIONAL MEDICAL IMAGE WORKFLOWS

(71) Applicant: Siemens Healthcare GmbH, Erlangen (DE)

(72) Inventor: Daphne Yu, Yardley, PA (US)

(73) Assignee: Siemens Healthcare GmbH, Erlangen (DE)

( * ) Notice: Subject to any disclaimer, the term of this patent is extended or adjusted under 35 U.S.C. 154(b) by 88 days.

(21) Appl. No.: 15/841,864

(22) Filed: Dec. 14, 2017

(65) Prior Publication Data

US 2019/0183451 A1    Jun. 20, 2019

(51) Int. Cl.
| | |
|---|---|
| *A61B 8/08* | (2006.01) |
| *G16H 30/00* | (2018.01) |
| *G16H 30/40* | (2018.01) |
| *G06F 16/25* | (2019.01) |
| *G06F 16/50* | (2019.01) |
| *G16H 50/20* | (2018.01) |

(52) U.S. Cl.
CPC .............. *A61B 8/08* (2013.01); *G06F 16/258* (2019.01); *G06F 16/50* (2019.01); *G16H 30/00* (2018.01); *G16H 30/40* (2018.01); *G06T 2210/41* (2013.01); *G16H 50/20* (2018.01)

(58) Field of Classification Search
CPC ......... A61B 8/08; G06F 16/258; G06F 16/50; G16H 50/20
See application file for complete search history.

(56) References Cited

U.S. PATENT DOCUMENTS

| | | | |
|---|---|---|---|
| 6,934,698 B2 | 8/2005 | Judd et al. | |
| 8,655,053 B1* | 2/2014 | Hansen | G06Q 10/10 |
| | | | 382/154 |
| 9,418,482 B1* | 8/2016 | Yang | G06T 19/006 |
| 2004/0068423 A1 | 4/2004 | Shaw | |
| 2008/0155468 A1 | 6/2008 | Rosander et al. | |
| 2010/0179428 A1* | 7/2010 | Pedersen | A61B 8/00 |
| | | | 600/443 |
| 2013/0139110 A1 | 5/2013 | Fang | |
| 2013/0329011 A1* | 12/2013 | Lee | G06T 19/20 |
| | | | 348/46 |
| 2014/0121158 A1* | 5/2014 | Bar-Or | G01N 27/4168 |
| | | | 514/5.9 |

(Continued)

OTHER PUBLICATIONS

Google Scholar Search Results.*

(Continued)

*Primary Examiner* — Qun Shen

(57) ABSTRACT

Systems and methods are provided for generating a two-dimensional image for identification of medical imaging data. An image processor acquires the medical imaging data and determines a category of the medical imaging data. A machine-learnt network identifies as a function of the category, a plurality of settings of rendering parameters that highlight one or more features the medical imaging data. The image processor renders the two-dimensional identifier image from the medical imaging data using the plurality of settings of rendering parameters and stores the medical imaging data with the two-dimensional identifier image.

17 Claims, 7 Drawing Sheets

(56) References Cited

U.S. PATENT DOCUMENTS

| | | | | |
|---|---|---|---|---|
| 2015/0106364 | A1* | 4/2015 | Schpok | G06F 16/58 |
| | | | | 707/724 |
| 2015/0142457 | A1* | 5/2015 | Marshall | G16H 50/50 |
| | | | | 705/2 |
| 2017/0007148 | A1* | 1/2017 | Kaditz | A61B 5/055 |
| 2017/0038951 | A1* | 2/2017 | Reicher | G06F 16/245 |
| 2017/0308656 | A1* | 10/2017 | Petkov | G06K 9/6262 |
| 2017/0345130 | A1* | 11/2017 | Wang | G06T 3/4046 |
| 2018/0068083 | A1* | 3/2018 | Cohen | G16H 50/30 |
| 2018/0137621 | A1* | 5/2018 | Stick | G06T 7/0012 |
| 2018/0342060 | A1* | 11/2018 | Yao | G06F 19/321 |

OTHER PUBLICATIONS

Extended European Search Report (EESR) dated May 13, 2019 in corresponding European Patent Application No. 18211572.5.
Anonymous "Thumbnail—Wikipedia", Dec. 10, 2015; XP055530066,; Retrieved from the Internet: URL:https://en.wikipedia.org/w/index.php?title= Thumbnail&oldid=694601304.

* cited by examiner

METHOD FOR MEMORABLE IMAGE GENERATION FOR ANONYMIZED THREE-DIMENSIONAL MEDICAL IMAGE WORKFLOWS

BACKGROUND

The present embodiments relate to processing medical diagnostic images.

For medical and clinical practice and research, imaging data may be collected and stored. One of the mechanisms to safeguard patients is to anonymize the imaging data. Anonymizing the data includes removing any identifying information about the individual patients in the data set, hence making the re-identification of those individuals very difficult. Anonymization of image data may be a compliance requirement for transfer of the data out of a hospital by software systems. In an example, medical data is anonymized inside the hospital network, and then transferred out to external systems, for example, a cloud network, to provide a more extensible information access point to the user, or to provide some software services that leverages cloud computing.

Anonymization of imaging data, however, causes issues for operators processing the imaging data. An operator may upload or transfer image data to an external system destination. The patient identifiable information, such as name, identifiers (IDs), or birthdates are removed. The removal of identifying information creates a cognitive challenge for the operator to remember to which patient the data that was uploaded belongs. Existing systems present the anonymized data back to the operator based on dates and ID numbers that may not be easily memorable. Mistakes due to the mental load and general fatigue of the operator may thus occur. For example, basic textual information such as IDs, dates or basic allowable information such as gender may require the operator to tediously read and sort out the information mentally.

BRIEF SUMMARY

By way of introduction, the preferred embodiments described below include methods and systems for alleviating problems caused by anonymization of medical imaging data. Memorable image thumbnails are automatically created using rendering parameters selected by a machine-learnt network. An operator may easily access the correct medical imaging data using the memorable image thumbnail without sacrificing privacy.

In a first aspect, a method is provided for generating a two-dimensional image for identification of medical imaging data. An image processor acquires the medical imaging data and determines a category of the medical imaging data. A machine-learnt network identifies as a function of the category, a plurality of settings of rendering parameters that highlight one or more features the medical imaging data. The image processor renders the two-dimensional identifier image from the medical imaging data using the plurality of settings of rendering parameters and stores the medical imaging data with the two-dimensional identifier image.

In a second aspect, a method is provided for generating a memorable image for identification of imaging data. An image processor acquires imaging data. A machine learnt network identifies a plurality of values of rendering parameters that highlight one or more features in the imaging data. The image processor identifies a plurality of values of reference parameters used to render a reference image. The image processor renders using the imaging data, the plurality of values of classification parameters, and the plurality of values of parameters, a two-dimensional image. The imaging data is stored with the two-dimensional image as an identifier.

In a third aspect, an imaging system is provided for generating a two-dimensional image for identification of medical imaging data. The system comprises a medical imaging scanner, a machine-learnt network, an image processor, and a datastore. The medical imaging scanner is configured to acquire a medical imaging data. The machine-learnt network is configured to identify one or more values of rendering parameters for rendering a two-dimensional image from the medical imaging data. The image processor is configured to render the two-dimensional image from the medical imaging data using the one or more values of rendering parameters. The datastore is configured to store anatomized medical imaging data with the two-dimensional image as an identifier.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Anonymization of medical imaging data may lead to confusion when attempting to access the medical imaging data. Embodiments provide a method and system to generate memorable image thumbnails to support an operator with easy recognition of the correct data without sacrificing privacy. Memorable features from medical imaging data are identified using a machine trained network. The memorable features are used to render a two-dimensional image. The two-dimensional image of the may be used as an identifier for the medical imaging data. A physician or clinical researcher may be more likely to connect a given image with a particular patient, so the use of the image as the identifier maintains anonymization while providing a correct linkage to a particular patient.

Anonymization of medical image data may be a compliance requirement for transferring or accessing medical data. After being collected or acquired, medical data may be anonymized locally, e.g. by a hospital network, and then transferred to external systems, such as a cloud, for storage or future access. An operator may be responsible for transferring or accessing medical data. For example, an operator may decide to store or access medical imaging data. For storage, the operator uploads or transfers the medical image data to an external system destination. In the process of uploading the medical image data, the patient identifiable information, such as name, IDs, or birthdates are removed. Anonymization (or removal of identifiable information) may take various forms. One method for anonymizing medical imaging data includes removing all patient identifying data and assigning the medical imaging data an ID code. ID codes may include a string of random or assorted alphanumeric characters.

When later attempting to access the medical image data, the newly anonymized data is presented back to the operator based on dates and ID numbers, which are not easily memorable. For an operator that manages scans of multiple patients and multiple sets of image data, the added mental load of remembering an alphanumeric string may be taxing.

Figure 1:
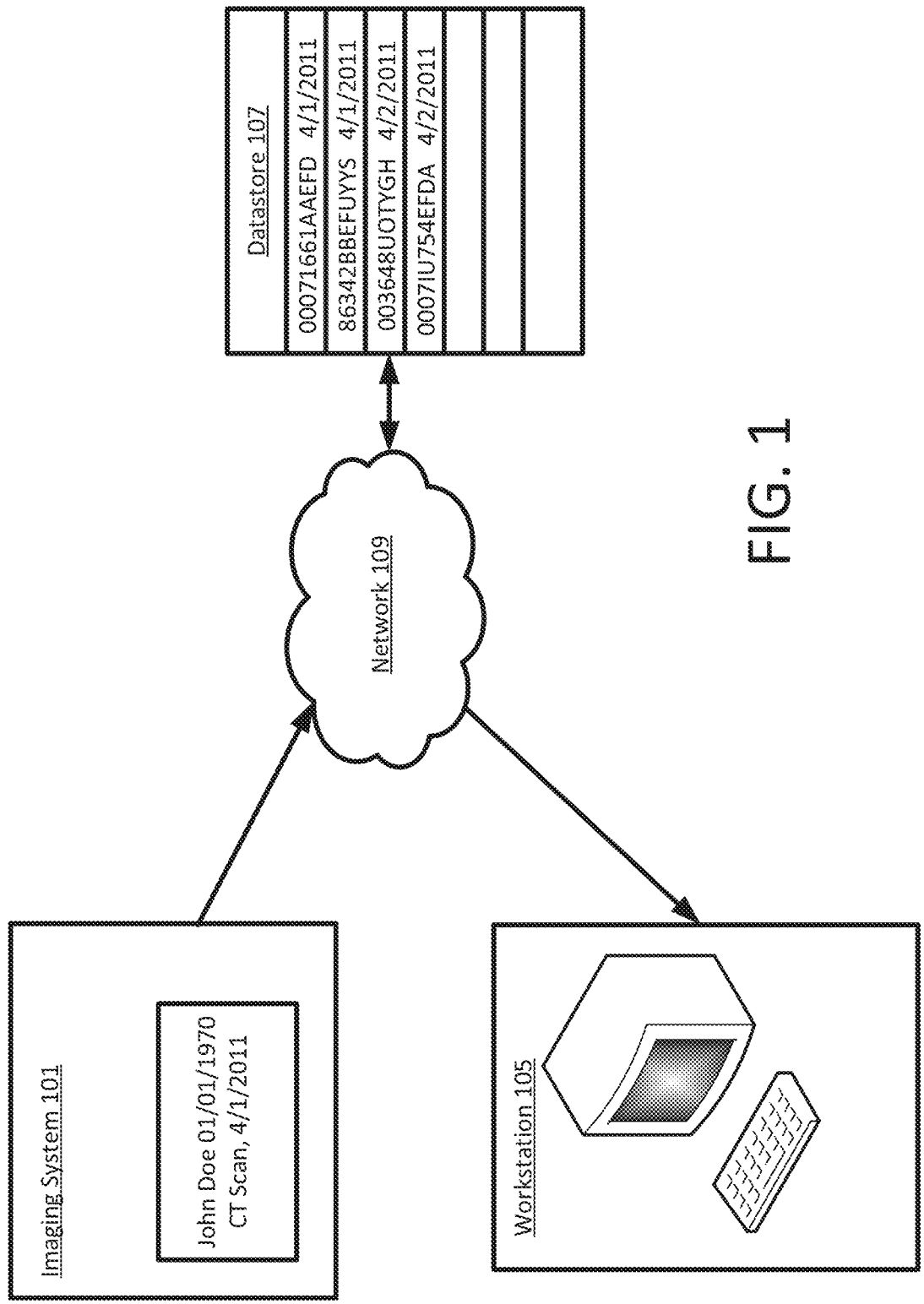
FIG. 1 depicts an example anonymization scheme using codes.

FIG. 1 depicts an example anonymization scheme using ID codes. Medical data is acquired using an imaging system 101 that includes some information that relates to a patient. The patient information may include, for example, the patient name, medical history, date of birth, etc. (e.g., John Doe Jan. 1, 1970, CT Scan of Apr. 1, 2011). Anonymization of the medical data removes the patient information that might identify the patient. The medical data is then assigned a unique ID code that identifies the patient and the anonymized medical data. The anonymous medical data may then be transmitted over a network 109 to a database 107. The anonymized medical data may be stored in the database 107 with ID code(s) for later use. To complicate the scheme further, each different collection of medical data, for example, each visit or each scan, may be stored separately. The additional collections may share the patient ID code with prior collections but add on an additional anonymized ID identifier to identify the additional visits or scans. When an operator at a workstation 105 desires to view or access the medical data, the operator needs to correctly select or input the various ID codes. The selected medical data is then transmitted over the network to the workstation 105. Due to the anonymization, the operator may not remember which dataset is stored under which ID, leading to downloading incorrect medical data in a waste of time, bandwidth, and/or processing.

Figure 2:
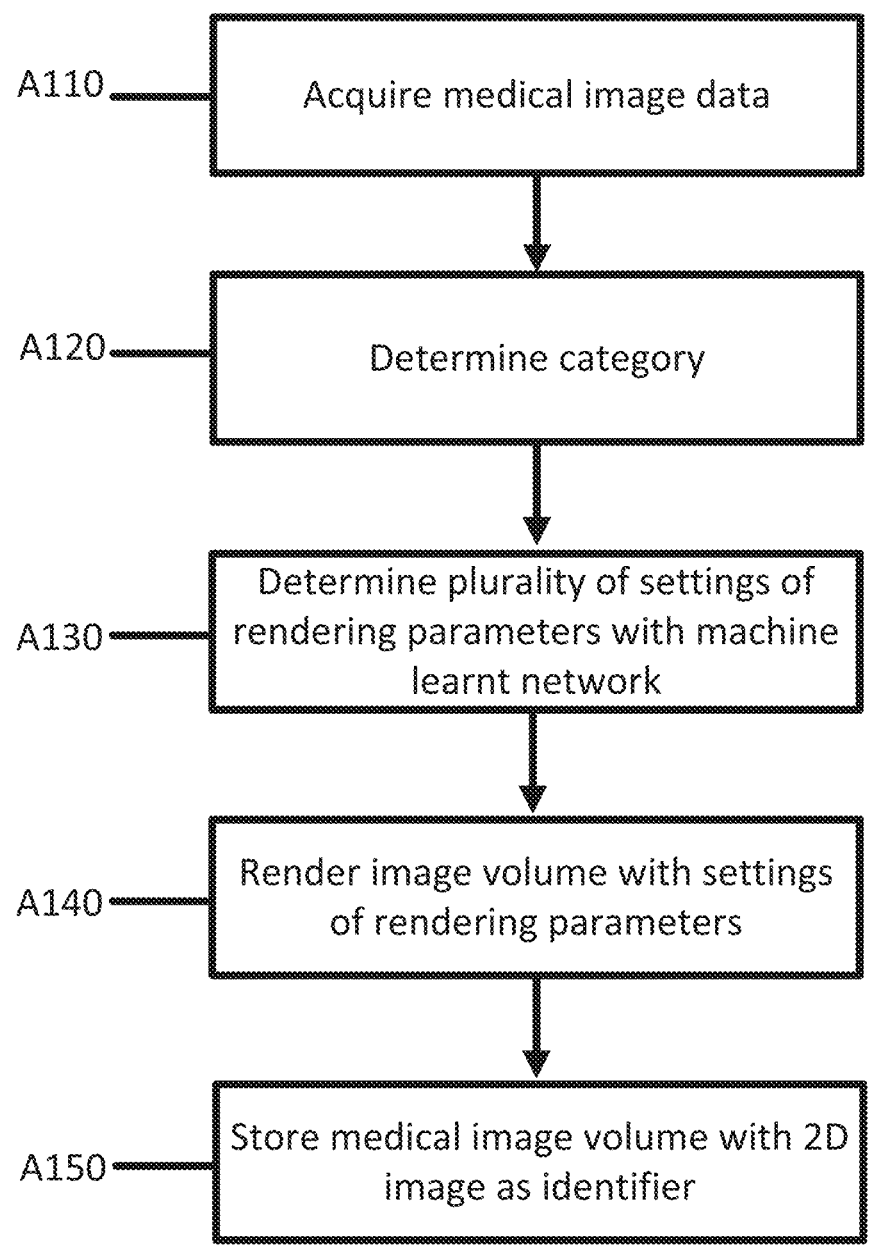
FIG. 2 depicts an embodiment of a method for providing a memorable image as an identifier for a medical imaging workflow.

FIG. 2 depicts one embodiment of a method for providing a memorable image as an identifier for a medical imaging workflow. In place of, or in addition to, an ID code, a two-dimensional image is provided with medical imaging data. The medical imaging data is rendered to include one or more features or aspects of the medical imaging data. A two-dimensional image is stored with the medical imaging data. Using the two-dimensional image, an operator may remember which medical imaging data applies and select the correct medical image data while still maintaining anonymization of the medical imaging data. For example, the operator may remember a patient for having a somewhat unique anatomical arrangement (e.g., the patient with the enlarged liver).

Figure 7:
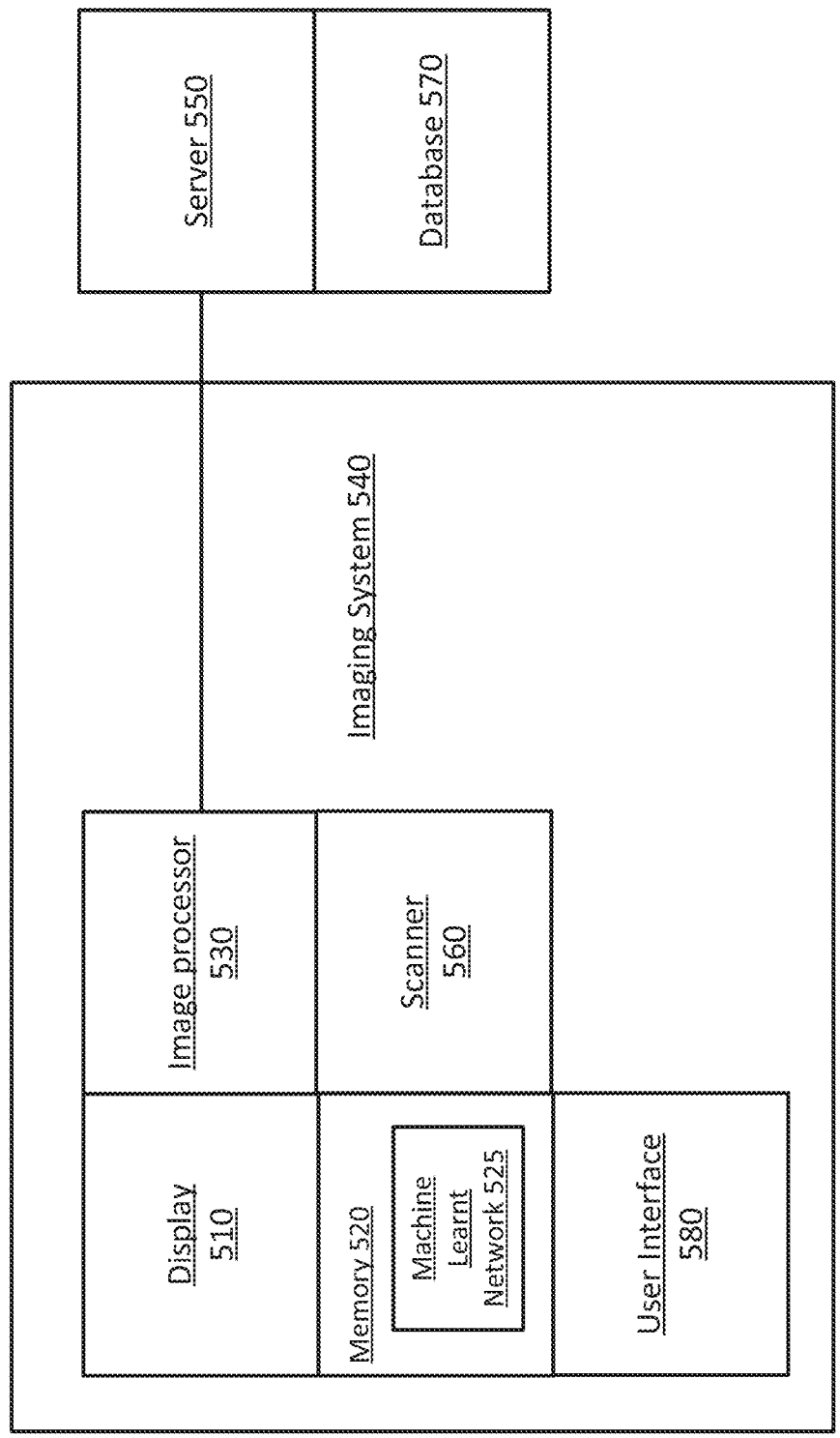
FIG. 7 depicts an embodiment of a system for generating a memorable two-dimensional image from medical imaging data.

The acts are performed by the system of FIG. 7, other systems, an image processor, a medical scanner, a workstation, a computer, and/or a server. For example, A110 may be performed by a medical imaging device. The other acts are performed by a processing component, such as an image processor, medical scanner, a workstation, a cloud based processing computing node, or simply a computer. Act 150 may be performed by a database or remote server. Additional, different, or fewer acts may be provided. The acts are performed in the order shown (e.g., top to bottom) or other orders.

At act A110, medical imaging data is acquired. Medical imaging data may be acquired from any modality such as computed tomography (CT), magnetic resonance imaging (MRI), dynaCT, ultrasound (US), positron emission tomography (PET), among others. The medical imaging data may be acquired from a remote terminal or database, after having been acquired by scanning.

The medical imaging data may be three dimensional or two dimensional. In one embodiment, the imaging data is CT images acquired with a CT system. For CT, the raw data acquired with the detector is reconstructed into a three-dimensional representation. In another embodiment, MRI data representing a patient is acquired. MRI data is acquired with an MRI system. The data is acquired using a pulse sequence and coils for measuring magnetic response. For MRI, the magnetic resonance data is k-space data. Fourier analysis is performed to reconstruct the data from the k-space into a three-dimensional object or image space.

In an example of medical imaging data acquisition, a patient is scanned by a medical imaging scanner. A region of the patient, e.g. an organ or object, may be manually or automatically selected. The medical imaging scanner acquires imaging data of the region or object using one or more modalities. The scan acquires data representing the patient, and as such may include information representing features of or in the scanned region or object. For example, the region may include non-anatomical objects, such as devices, implants, stents, air or intravenous tubes, or bandages. Other features of the region may include features such as embolisms, large tumors, visible trauma such as broken bones, etc. Other more natural memorable features might also be the general shape and size of the object. Similar organs for different patients may exhibit different dimensions or shapes. Each of the features may describe a distinction between the scanned region or object and a canonical healthy region or object. In each case, the acquired medical imaging data may differ from medical imaging data of a canonical healthy body of the same gender. Rendering parameters may be selected to highlight such features in a two-dimensional thumbnail image.

At act A120, the image processor identifies a category of the medical imaging data. The category of the medical imaging data may describe one or more parameters of the scan. The category may relate to a canonical reference data that includes a similar representation of the patient. The category may thus identify a type, modality, region, etc. of the canonical reference data. An example of a category may be: a CT scan of a patient's lower GI tract. The category may be selected automatically based on scan parameters. For example, a scan performed on an organ may include scan parameters that identify the modality, the region, the organ, the field of view etc. (e.g., using scan parameters available in associated metadata). The medical imaging system may automatically assign the category based on the scan parameters. Alternatively, the category may also be selected by an operator, or by other automatic or semi-automatic post processing algorithms. In an embodiment, the categorization step may not be performed. If the category is available, the identification of the category may facilitate the accuracy of the subsequent selection of rendering parameters with the machine learnt network.

At act A130, a machine-learnt network, as a function of the category, identifies a plurality of settings of rendering parameters that highlight one or more features of the medical imaging data. The machine-learnt network is any type of machine-learnt network that receives an input set of medical imaging data and outputs one or more rendering parameters. Rendering parameters may include settings or values that are used for rendering a two-dimensional image from the acquired medical imaging data. Example of rendering parameters include lighting, texture, shading, contrast, specularity, material property, window, and transfer function (color), clipping, among others.

For training the machine-learnt network, regression, classification, and/or other learning may be used. Regression learns a range or continuous output by minimization of a metric. Classification learns disparate outputs. Support vector machine, Bayesian network, a probabilistic boosting tree, neural network, sparse auto-encoding classifier, or other now known or later developed machine learning may be used. Any semi-supervised, supervised, or unsupervised learning may be used. Hierarchal, cascade, or other approaches may be used.

In an embodiment, a neural network (e.g., deep neural network) is used. For a neural network, the network learns the features of the input data to extract from the training data. The training relates the input image data to the rendering parameters through one or more layers. One layer may relate feature values to the class. For deep-learnt networks, there may be further layers creating further abstract features from outputs of previous layers. The resulting machine-trained network is a matrix for inputs, weighting, and combination to output rendering parameter settings to generate a two-dimensional image that is memorable.

In an embodiment, a deep learning network is trained using deep regression learning. The deep learning network is trained using a collection of acquired medical imaging data. The acquired medical imaging data may be sorted into categories by scan modality, gender, body type, scanned region (or object), a field of view, etc. The categories for the training images may be the same or similar to the categories defined in act A120 described above. Body size or general field of view of the image data may be detected automatically using a body region detector or manually by an operator.

For training of the deep learning network, the collection of medical imaging data is input into the deep learning network. The deep learning network identifies values for rendering parameters that, when used to render a set of medical imaging data, generates a memorable image that may be used to identify the medical imaging data. The rendering parameters may include parameters such as lighting, texture, shading, contrast, specularity, material property, window, and transfer function (color), clipping, among others.

A level of clipping, for example, may be identified by the machine-learnt network. Clipping, for example, may expose the interior of an organ by turning one or more voxels transparent or translucent. The machine-learnt network may identify which if any clipping might occur to generate a memorable image. In an example, clipping may determine which features are visible in the output image. The machine-learnt network may identify that one feature is more memorable in the medical imaging data and as such may be included in the output image than another feature that may be obscured in the medical imaging data and not depicted in the output image.

The deep learning network may be used to improve the robustness of the produced rendering parameters, e.g. to reduce sensitivity to different pose, different patient variations, fields of view and scan parameters of the data.

Figure 3:
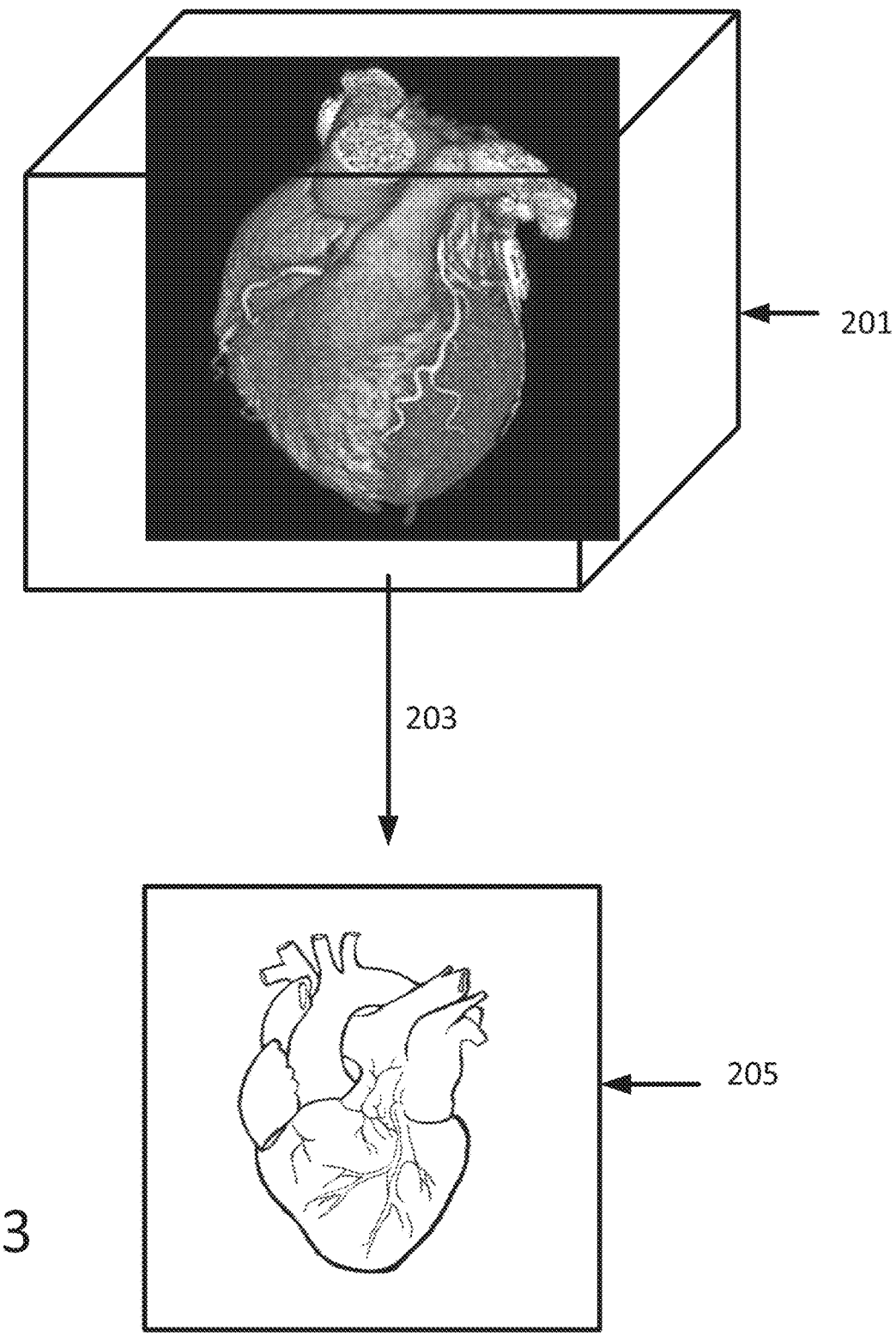
FIG. 3 depicts example reference medical imaging data and a reference two-dimensional image.

In an embodiment, the training data may include canonical reference medical imaging data and a collection of medical imaging data. FIG. 3 depicts an example canonical reference medical imaging data 201 and reference two-dimensional image 205. The canonical reference medical imaging data 201 is rendered 203 using selected settings of reference rendering parameters to produce the reference image 205. The reference image 205 is created using reference parameters that provide a representative depiction of the category. The reference settings of the rendering parameters may provide that any input image data in the category that is rendered with the reference settings of the parameters may maintain a resemblance to the reference image 205. An operator may be able to recognize the category even if other rendering parameters have been adjusted. The reference settings of the parameters may include rendering parameters such as lighting, texture, shading, contrast, specularity, clipping, window, material properties, and colors, among others. To generate a reference image 205, different sets of settings of rendering parameters may be used to render multiple potential reference images.

The canonical reference medical imaging data 201 may be selected automatically or may be the result of a scoring or selection process. For example, for each different category, multiple canonical reference medical imaging data may be identified. Operators may select the canonical reference medical imaging data that is most representative of the category. Alternatively, the canonical reference medical imaging data may be selected automatically.

The reference image 205 may depict a snapshot of the reference input image data 201. The reference input image data may include more information that may be seen from a different angle by a viewer. The reference image 205 may only depict what a viewer may see from a single angle. For example, the canonical reference medical imaging data 201 may include data relating to unseen voxels, e.g. portions of the interior of the image data. Clipping may be used to expose the interior portions. The reference image 205 may, as such, be able to depict portions of the interior of the object. The portions that are clipped may be determined automatically as a function of the selected rendering parameters. The clipping may be performed during the rendering process or may be performed on the canonical reference medical imaging data 205 prior to rendering the two-dimensional image.

For training, a collection of medical imaging data is acquired for similar types of scans. The collection of medical imaging data may include different features (such as foreign objects or distinct anatomy). For each set of medical imaging data, a variety of rendering parameters are automatically selected (while keeping other rendering parameters consistent). The rendering parameters are then applied to the medical imaging data pool to produce a series of rendered images for each set of medical imaging data. In an embodiment, operators may visually select the produced images that are the most memorable and unique images in relation to the respective input medical imaging data. The rendering parameters for the selected images are used as the desired output to train the network.

The operators may score each produced image for memorability. Any scoring may be used. For example, a numerical range representing how memorable an image is, such as 1-5 or 1-10, where the larger or smaller number represents a more memorable image. As another example, alphanumeric classes are used, such as poor memorability or good or such as poor, below average, average, good, or excellent memorability. Scores may be generated by presenting images produced from different inputs and letting operators attempt to match the produced images with the input medical imaging data. The images that are matched correctly may be assigned a higher score.

Figure 4:
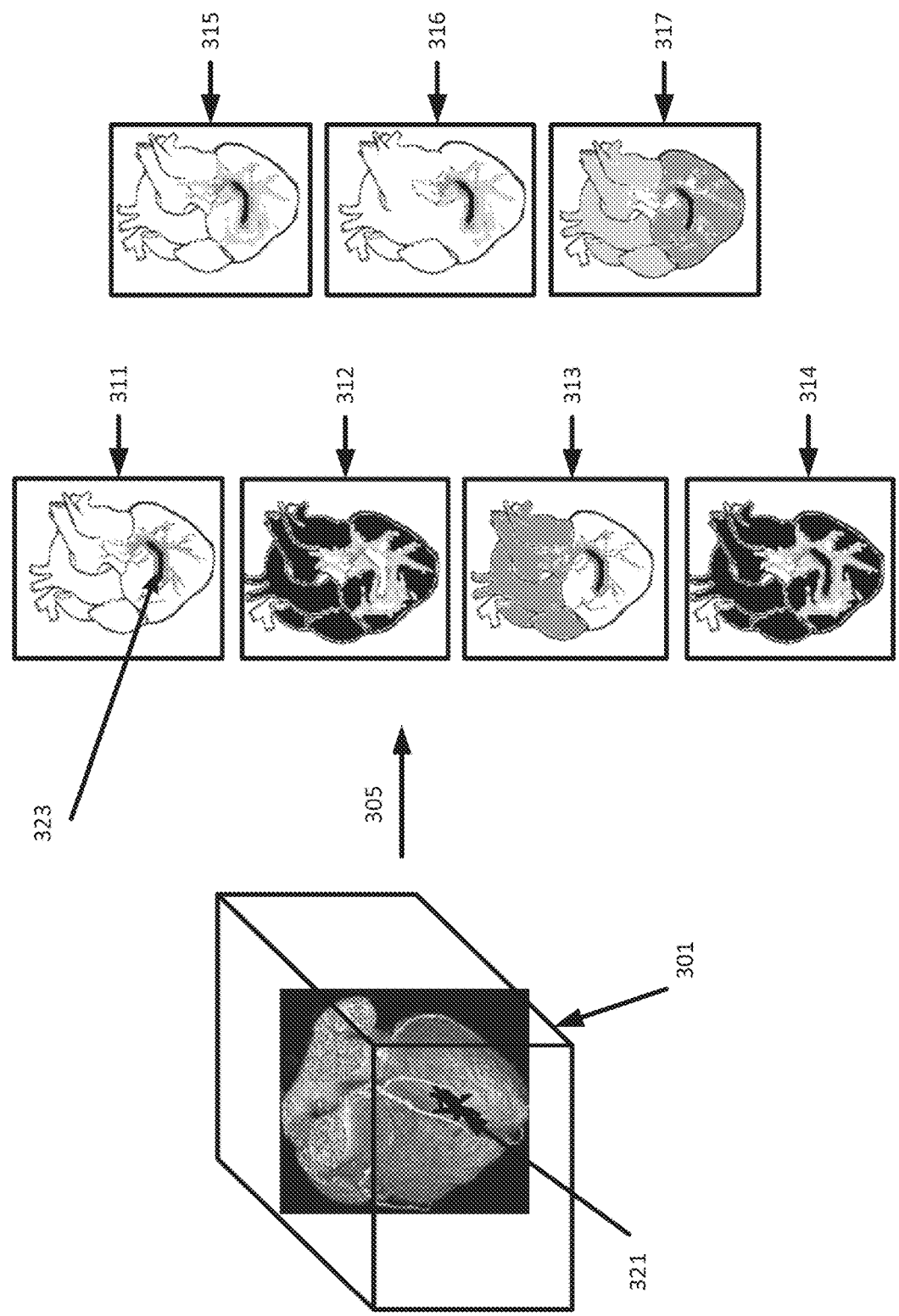
FIG. 4 depicts example training medical imaging data and example generated two-dimensional images.

FIG. 4 depicts a training set of medical imaging data 301 and seven rendered two-dimensional images 311-317. The two-dimensional images 311-317 may be rendered using different settings of rendering parameters. In an embodiment, the rendering parameters may be combined with a group of settings of reference parameters used to generate a reference image for the category from the canonical reference medical imaging data. The group of settings of the reference parameters may provide a rendering that maintains a similar depiction over the entire category. For example, the reference parameters may include a setting for clipping or size. As each of the two-dimensional images 311-317 may be rendered 305 with similar or same settings of the rendering parameters as the reference image 205 for the category of training image data, each resulting rendered image may appear similar. For example, each of the two-dimensional images 311-317 maintain a similar size and shape. An operator observing the two-dimensional images 311-317 may be able to discern that the medical imaging data belonged to the same type of medical imaging data as others in the category. The settings for one or more other rendering parameters for the two-dimensional images 311-317, however, are different for each two-dimensional image 311-317. For example, for two-dimensional image 311, 315, and 316, portions of the tissue are not shaded, while for references 312 and 314, the tissues are shaded a dark black. One feature that distinguished the medical imaging data 301 and healthy medical imaging data is a feature 321, for example, scar tissue. An operator, when performing the scan, may remember the feature for the patient and the scan. Accordingly, the two-dimensional images 311-317 may highlight or distinguish the feature, for example, by darkening or highlighting the feature 323 as in image 311. While seven two-dimensional images are depicted, there may be hundreds, thousands, or more possibilities as each setting of rendering parameters, e.g. shading, lighting, or contrast may include multiple different values.

For training the machine-learnt network, each of the generated two-dimensional images 311-317 may be manually assigned a score. For example, on a 1-5 score (5 being the most memorable), two-dimensional image 311 may score a 4, while two-dimensional image 317 may score a 5. The scores for each of the generated two-dimensional images 311-317 and the settings of rendering parameters that generated the two-dimensional images 311-317 are used as training data along with the input image data to teach the machine-learnt network to identify settings of rendering parameters that generate memorable results. The training may be repeated or checked periodically by an operator, for example, by updating the training data or reevaluating the scores.

In another embodiment, the training uses a metric to evaluate each rendered two-dimensional image 311-317 in comparison with the reference two-dimensional image 205. For each set of generated settings of rendering parameters, the canonical medical imaging data and a training set of medical imaging data are rendered into two-dimensional images. The metric is applied to the pair of two-dimensional image outputs to compare the two-dimensional images. The training uses a metric of difference between a reference image and an image generated with the parameters. Any metric of difference may be used. Example computed metrics may be visual perception metrics based on visual systems, comparative differences, perceptual hash, mutual information, correlation, computed feature signals, or simple error metrics. The metrics may be automatically computed or provided by the users. The metric is used as an indicator of strength of importance of a given training sample.

The metric may include a scoring mechanism. A high score may indicate that the training two-dimensional image highly differs from the reference two-dimensional image. Higher scores for one training two-dimensional image than another training two-dimensional image indicate that the first two-dimensional image differs more from the reference two-dimensional image than the second two-dimensional image. In order to prevent empty or null images, the settings of the rendering parameters may be selected to maintain at least some semblance to the reference image. One metric that may be used is a perceptual image metric robust to color perception. The metric is used as a reward to train the deep learning network towards the two-dimensional image that is most different from the reference and the respective setting of the rendering parameter regarded as the desired output. Using the input images, medical imaging data, settings of rendering parameters, and the metrics or manual scores, the deep learning network is trained to identify one or more settings of parameters for rendering a two-dimensional image that is distinct and/or memorable.

The training may be repeated. As the machine-trained network is used, the user may adjust some of the output settings. The adjustment, the setting, and/or image resulting from the adjustment are added to the training data. The machine learning network is refined by repeating the learning with the addition feedback as samples from which to learn. The manually adjusted settings of the parameters define personalized visualization designs. Other sources of further training data may be used.

The repetition of the training may be performed separately for different users, physicians, medical groups, hospitals, or other grouping. Personalized training may be used so that consistent images for a relevant group are provided. In other embodiments, the repetition is provided for all users. Different machine-learnt networks may be trained and used for different categories of images.

A feedback mechanism may be used to update the machine-trained network. When accessing stored data using a two-dimensional image, if the correct medical imaging data is accessed, a score of the two-dimensional image may be increased, while if the wrong medical imaging data is accessed, the respective two-dimensional image score may be decreased. The training data may be updated with the updated scores periodically to improve the accuracy of generating settings of rendering parameters that result in a memorable identifier image.

The medical imaging data and the category is input into the machine learnt network. The output of the machine learnt network is a plurality of settings of rendering parameters that highlight one or more features of the medical imaging data. The rendering parameters may include settings or values for lighting, texture, shading, contrast, specularity, material property, window, and transfer function (color), clipping, among others.

At act A140, the image processor renders the medical imaging data using the plurality of settings of rendering parameters to produce a unique two-dimensional identifier image. The settings of rendering parameters may include parameters such as lighting, texture, shading, contrast, specularity, window, material properties, clip plane position, camera position, and/or colors, among others. The settings for the rendering parameters may highlight the unique features of the medical imaging data. For viewing the features in context, the selected settings of the rendering parameters may be merged with the reference settings of the rendering parameters used to render a reference image into one final set of settings of rendering parameters. Merging the parameters may be accomplished using a matrix, by parameter by parameter array interpolation between the two parameter sets, or other types of linear interpolation between the parameter function values. Merging of the parameters provides a group of settings for rendering an identifier image that represents both the category (for a first level identification) and the specific features of the medical imaging data (for a second level patient specific identification). The reference parameter settings may indicate to the operator the type of scan, and the rendering parameters settings may indicate the specific patient or organ that was examined. The operator may thus be able to differentiate different categories of scans and also different patients when selecting from multiple different sets of image data.

In an embodiment, the settings of the rendering parameters may be weighted more heavily than the settings of the reference parameters in order to emphasize the features. The result rendered from the combined settings is an image that may both capture the unique features of the medical imaging data in addition to the reference features in context such that the category of medical imaging data may also be easily identified. In an example, medical imaging data is acquired that represents an abdomen CT scan. The medical imaging data may be rendered with parameters that generate a canonical view of an abdomen. In the medical imaging data, unique features in the regions may include tubes on the surface of the body or devices previously embedded from procedures. The foreign objects may be identified by the machine-learnt network and highlighted by settings for one or more rendering parameters. The output settings are used with the reference settings to render an image. The rendered foreign objects may be added to the general abdomen view to generate a rendered two-dimensional image that may be used to assist fast association of corresponding data when the data has been de-identified to facilitate accurate workflow without sacrificing privacy.

The output of the rendering process is a unique two-dimensional image. Because the input is the unique medical imaging data from a scan of a patient, the outputted two-dimensional image, even with the same settings of rendering parameters as another workflow, will be unique. The view of the two-dimensional image may be determined by the canonical view of the category. For example, for one category, the canonical reference view may be an isometric view with a portion of an organ clipped away. The two-dimensional image may retain the isometric view with similar clipping to convey to an operator the category or type of medical imaging data. In another category, the canonical reference view may be an image slice of an object.

The two-dimensional image may be rendered to be reduced in size to be easily shown to an operator. For example, the two-dimensional image may have a resolution of 75×75, 100×100, 125×125, 150×150, or 200×200 pixels. The image may be formatted using any image format such as .JPG, .GIF, .BMP, or .PNG. In an embodiment, the two-dimensional image may remain under a 0.5, 1, or 2 MB limits to conserve resources. In an embodiment, the two-dimensional image may be color or black and white. In an embodiment, the two-dimensional image may be a thumbnail image.

At act A150, the medical imaging data is stored with the two-dimensional identifier image. The acquired medical imaging data may be stored for later analysis in a memory or database, for example, using a Digital Imaging and Communication (DICOM) standard. In an embodiment, the medical imaging data may be transmitted remotely for storage or analysis.

To access the medical imaging data, an operator may use any application that allows access to medical imaging data. The medical imaging data may be accessed by the user by selecting the two-dimensional identifier image.

Figure 5:
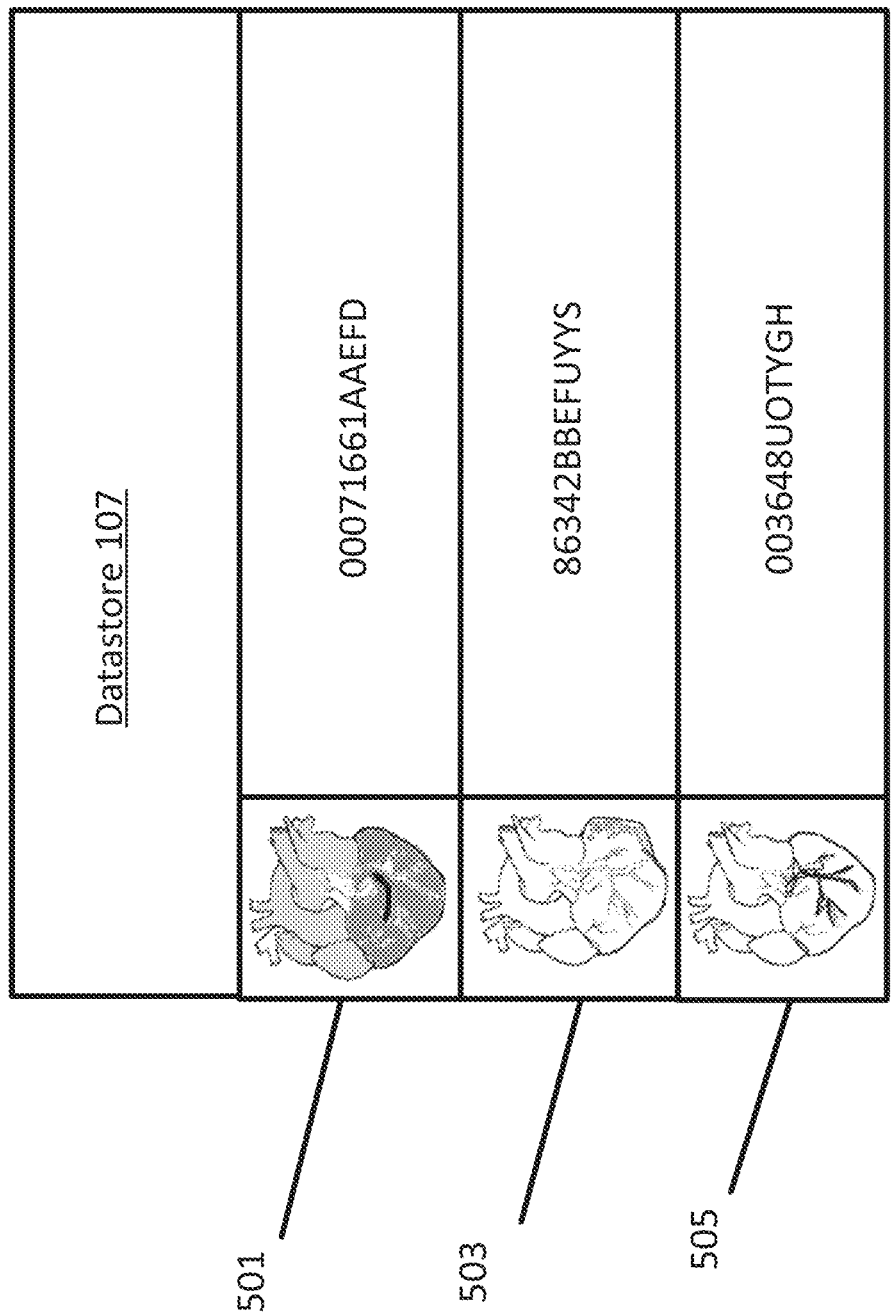
FIG. 5 depicts an example interface for accessing stored anonymized medical imaging data.

FIG. 5 depicts an example interface for accessing stored anonymized medical imaging data. FIG. 5 includes three different groups of medical imaging data 501, 503, 505. Each group may correspond to a different medical imaging scan. The medical imaging data 501, 503, and 505 has been anonymized, e.g. patient identifying information has been removed and replaced with a ID code. In addition to the ID code (or replacing the ID code), each group of medical imaging data 501, 503, and 505 includes a thumbnail image generated at act A150. As depicted the thumbnail for 501 is the thumbnail selected in FIG. 4 as being the most memorable. An operator may access the datastore 107 to access medical data relating to a particular scan. The operator may remember features from the scan that are now depicted in the thumbnail image. The operator may thus easily and correctly select the desired medical imaging data.

Figure 6:
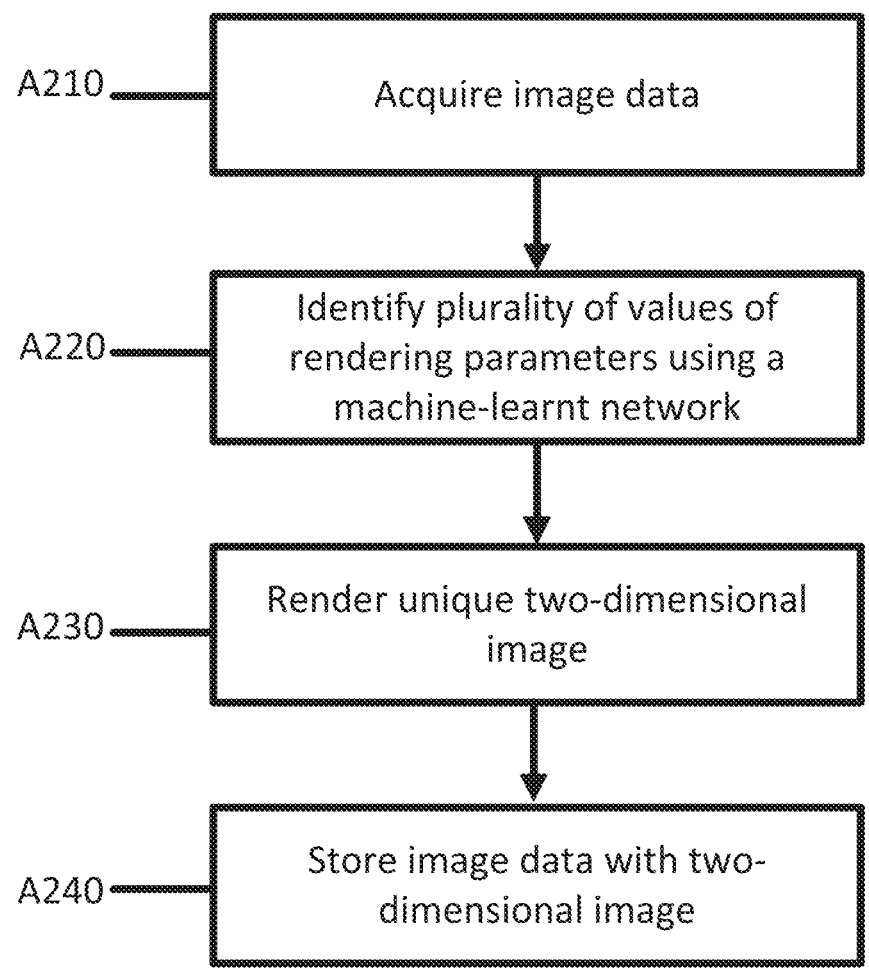
FIG. 6 depicts an embodiment of a method for generating a memorable two-dimensional image for identification of imaging data.

FIG. 6 depicts an embodiment of a method for generating a memorable two-dimensional image for identification of imaging data. The method of FIG. 6 may apply to any imaging data. The imaging data is rendered using both settings from a reference set of imaging data and a machine learnt group of setting.

The acts are performed by the system of FIG. 7, other systems, a medical scanner, a workstation, a computer, and/or a server. For example, acts A220-A240 are performed by a processing component, such as a workstation or a computer. Act A210 may be performed by an imaging device. The acts are performed in the order shown (e.g., top to bottom) or other orders. Additional, different, or fewer acts may be used, such as not performing A210 if the imaging data has been previously acquired from an imaging device.

At act A210, imaging data is acquired. The imaging data may be a collection of one or more slices of imaging data captured from a scanning device. The medical imaging data may include three dimensions of imaging data. In one embodiment, the imaging data is acquired with a CT system. For CT, the raw data acquired with the detector is reconstructed into a three-dimensional representation. In another embodiment, MRI data representing a patient is acquired. MRI data is acquired with an MRI system. The data is acquired using a pulse sequence and coils for measuring magnetic response. For MRI, the magnetic resonance data is k-space data. Fourier analysis is performed to reconstruct the data from the k-space into a three-dimensional object or image space. The method is not limited to CT and MR imaging modalities, other acquisition system may also be used. The medical imaging data may be previously acquired and stored.

At act A220 a plurality of values of rendering parameters that highlight one or more features in the imaging data are identified by a machine-learnt network. The plurality of values of rendering parameters may be learnt by training the machine learnt network on a collection of previously acquired imaging data. The previously acquired imaging data is rendered using a variety of values of rendering parameters. An output rendered two-dimensional image is scored for either memorability or distinctness from a canonical reference image. In order to provide consistency across the outputted rendered two-dimensional image, the values of rendering parameters may be combined with one or more values of reference parameters. The values of reference parameters may be determined by rendering the canonical reference image. The combination of rendering and reference parameters provides similar, yet still distinct outputted two-dimensional images. Combining the values of parameters may use linear interpolation.

The canonical reference image and reference imaging data from which the reference image was rendered may be selected automatically or manually by an operator. The reference imaging data may include imaging data that has been designated as a standard for a category of imaging data. For example, healthy imaging data of a heart acquired using a specific modality from a specific angle for this type of scan may be used as the healthy imaging data. The reference image data may be an actual image data captured from a scan. The reference image data may be a construct, for example generated from multiple scans or artificially to provide a typical image of the region specified by the category.

At act A230, the image processor renders a unique two-dimensional image that highlights the plurality of features using the imaging data, the plurality of values of classification parameters, and the plurality of values of parameters. The two-dimensional image may be rendered as a thumbnail image.

At act A240, the image data is stored with the two-dimensional image as an identifier. The image data may be stripped of all identifying personal information. The two-dimensional image may be used by an operator to select the correct image data.

FIG. 7 depicts an embodiment of a system for generating a memorable two-dimensional image from a medical image volume. The system includes an imaging system 540, a server 550, and a database 570. The imaging system includes an image processor 530, a memory 520, a display 550, and a scanner 560. Additional, different, or fewer components may be provided. For example, network connections or interfaces may be provided, such as for networking with a medical imaging network or data archival system. In another example, the user interface 580 is provided as part of the display 510 or imaging system 540.

The image processor 530, memory 510, display 510, user interface 580, and scanner 560 are part of the imaging system 540. Alternatively, the image processor 530 and memory 520 are part of an archival and/or image processing system, such as associated with a medical records database workstation or server, separate from the imaging system 540. In other embodiments, the image processor 530 and memory 520 are a personal computer, such as desktop or laptop, a workstation, a server, a network, or combinations thereof. The image processor 530, display 510, and memory 520 may be provided without other components for acquiring data by scanning a patient.

The imaging system 540, image processor 530, memory 520, display 550, user interface 580, and scanner 560 are provided at a same location. The location may be a same room, same building, or same facility. The devices are local relative to each other and are remote to the server 550. The server 550 is spaced apart by a network by being in a different facility or by being in a different city, county, state, or country. The server 550 and database 570 may be remote from the location of the imaging system 540.

The imaging system 540 is a medical diagnostic imaging system. Computed tomography (CT), X-ray, ultrasound, and/or magnetic resonance (MR) systems may be used. The scanner 560 may include a transmitter and includes a detector for scanning or receiving data representative of the interior of the patient. The imaging system 540 is configured to acquire an image volume. The imaging system 540 may acquire a plurality of image volumes over time that may be used to generate a video.

In one embodiment, the imaging system 540 is a CT or X-ray system. An X-ray source is connected with a gantry. A detector is also connected with a gantry opposite the X-ray source. The patient is positioned between the source and detector. The source and detector are on opposite sides of the patient and rotate and/or translate about the patient. The detected X-ray energy passing through the patient is converted, reconstructed, or transformed into data representing different spatial locations within the patient. In an embodiment, the imaging system 540 may include a portable or mobile C-arm. The C-arm includes an X-ray source and an image intensifier or flat-panel detector. The C-shaped connecting element allows movement horizontally, vertically and around the swivel axes, so that X-ray images of the patient may be produced from almost any angle. The generator emits X-rays that penetrate the patient's body. The image intensifier or detector converts the X-rays into a visible image displayed on a monitor or stored for later use.

In another embodiment, the imaging system 540 is an MR system. The MR system includes a main field magnet, such as a cryo-magnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The memory 520 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 520 is part of the imaging system 540, part of a computer associated with the processor 530, part of a database, part of another system, a picture archival memory, or a standalone device.

The memory 520 stores medical imaging data, graphical or display setting, and/or images. The memory 520 may store data during processing for application and/or may store training data for a machine-learnt network 525.

The memory 520 or other memory is alternatively or additionally a non-transitory computer readable storage medium storing data representing instructions executable by the programmed image processor 530 for generating a memorable image. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 530 is a general processor, central processing unit, control processor, graphics processing unit, digital signal processor, three-dimensional rendering processor, image processor, application specific integrated circuit, field programmable gate array, digital circuit, analog circuit, combinations thereof, or other now known or later developed device for rendering a two-dimensional image from an image volume. The processor 530 is a single device or multiple devices operating in serial, parallel, or separately. The processor 530 may be a main processor of a computer, such as a laptop or desktop computer, or may be a processor for handling some tasks in a larger system, such as in the imaging system 530. The image processor 530 is configured by instructions, design, hardware, and/or software to perform the acts discussed herein.

The image processor 530 and/or server 550 are configured to perform the acts discussed above for generating a memorable two-dimensional image. The image processor 530 is configured to generate the memorable two-dimensional image using settings for the rendering parameters identified by the machine-learnt network 525.

The machine-learnt network 525 is trained using image volumes and a scoring mechanism that scores rendered two-dimensional images on how memorable the images are, e.g. how well an operator matches the rendered two-dimensional images to a correct respective image volume. Alternatively, the machine-learnt network 525 may be trained using the image volumes and a metric that measures a difference between a rendered two-dimensional image and a reference two-dimensional image rendered from a canonical image volume. The image processor 530 and/or server 550 may be configured to strip patient identifying information from the image volume (e.g. anonymization) and store the image volume in the database 570 using the rendered two-dimensional image as an identifier.

The image processor 530 and/or server 550 are configured to provide the image volume to the display 510 or to the memory 520. The display 510 is a monitor, LCD, projector, plasma display, CRT, printer, or other now known or later developed devise for outputting visual information. The display 510 receives images, graphics, text, quantities, or other information from the image processor 530, memory 520, imaging system 540, and/or server 550. The display 510 is configured to provide image volumes to an operator.

The user interface 580 may be configured to receive one or more selections from a user. The user interface 580 may include an input device such as one or more buttons, a keypad, a keyboard, a mouse, a stylus pen, a trackball, a rocker switch, a touch pad, a voice recognition circuit, or other device or component for inputting data. The user interface 580 and the display 510 may be combined as a touch screen that may be capacitive or resistive. The user interface 580 may be configured to receive a selection of a two-dimensional image and transmit a request to access the image volume associated with the two-dimensional image.

The server 550 connects to the imaging system 540 via a network. The network is a local area, wide area, enterprise, another network, or combinations thereof. In one embodiment, the network is, at least in part, the Internet. Using TCP/IP communications, the network provides for communication between the image processor 530 and the server 550. Any format for communications may be used. In other embodiments, dedicated or direct communication is used.

The server 550 is a processor or group of processors. More than one server 550 may be provided. The server 550 is configured by hardware and/or software.

The database 570 is a memory, such as a bank of memories, for storing data such as anonymized image volumes and two-dimensional images. The database 570 may be located locally or remotely.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for generating a two-dimensional image for identification of medical imaging data, the method comprising:
    acquiring, by an image scanner, the medical imaging data;
    determining, by an image processor, a category of the medical imaging data;
    identifying, using a machine-learnt network, as a function of the category, a plurality of settings of rendering parameters that highlight one or more features the medical imaging data, wherein the machine-learnt network is trained using an operator assigned memorability score generated by presenting images produced with different rendering parameters to operators and attempting by the operators to match the produced images with previously identified features, wherein images that are matched correctly are assigned a higher score;
    rendering, by the image processor, a two-dimensional identifier image from the medical imaging data using the plurality of settings of rendering parameters; and
    storing the medical imaging data with the two-dimensional identifier image.

2. The method of claim 1, wherein the medical imaging data comprises computed tomography scan data.

3. The method of claim 1, wherein the category is determined by modality, by gender of a patient, by approximate body size, and/or by a field of view of the medical imaging data.

4. The method of claim 1, wherein the machine-learnt network is trained using a metric selected to provide a higher score for rendered image data that differ the most from a rendered canonical reference data.

5. The method of claim 4, wherein canonical reference data comprises medical imaging data of a healthy patient.

6. The method of claim 4, wherein canonical reference data comprises artificially generated imaging data of a standard patient.

7. The method of claim 6, wherein the metric is selected to provide a higher score for nonempty rendered image data that differ from the rendered canonical reference data.

8. The method of claim 1, wherein the two-dimensional identifier image is a thumbnail image.

9. A method for generating a memorable image for identification of imaging data, the method comprising:
acquiring, by an image scanner, imaging data;
identifying, using a machine-learnt network, a plurality of values of rendering parameters that highlight one or more features in the imaging data, the machine-learnt network trained using an operator assigned memorability score generated by presenting images produced with different rendering parameters to operators and allowing the operators to attempt to match the produced images with the input medical imaging data, wherein images that are matched correctly are assigned a higher score;
identifying, by an image processor, a plurality of values of reference parameters used to render a reference image;
rendering, by the image processor using the imaging data, the plurality of values of rendering parameters, and the plurality of values of reference parameters, a two-dimensional image; and
storing the imaging data with the two-dimensional image as an identifier.

10. The method of claim 9, wherein rendering comprises:
rendering the imaging data with a combination of the plurality of values of rendering parameters and the plurality of values of reference parameters, wherein the plurality of values of rendering parameters and the plurality of values of reference parameters are combined using linear interpolation.

11. The method of claim 10, wherein the plurality of settings of rendering parameters are weighted more heavily than the plurality of values of reference parameters.

12. The method of claim 9, further comprising:
providing, the imaging data to an operator, when the two-dimensional image is selected.

13. The method of claim 9, wherein the machine-learnt network is trained using a metric selected to provide a high score for rendered two-dimensional images that differ most from a rendered reference image; wherein the metric is used as a reward to train the machine-learnt network.

14. A system for generating a two-dimensional image for identification of medical imaging data, the system comprising:
a medical imaging scanner configured to acquire medical imaging data;
a machine-learnt network trained using a metric for rendered two-dimensional images that relates to a memorability score of the rendered two-dimensional images generated by presenting images produced with different rendering parameters to operators and allowing the operators to attempt to match the produced images with the input medical imaging data, the machine-learnt network configured to identify one or more values of rendering parameters for rendering a two-dimensional image from the medical imaging data;
an image processor configured to render the two-dimensional image from the medical imaging data using the one or more values of rendering parameters; and
a datastore configured to store the medical imaging data with the two-dimensional image as an identifier.

15. The system of claim 14, wherein the medical imaging scanner is a computed tomography scanner.

16. The system of claim 14, wherein the machine-learnt network is trained using to provide a high score for the metric for rendered two-dimensional identifier images that differ most from a rendered reference image.

17. The system of claim 14, wherein the image processor is further configured to anonymize patient identifying data acquired with the medical imaging data.

* * * * *